US012753133B2

(12) United States Patent
Liu et al.

(10) Patent No.: US 12,753,133 B2
(45) Date of Patent: Oct. 6, 2026

(54) α-OLEFIN EXTRACTANT AND METHOD FOR SEPARATING AN ALKANE AND AN α-OLEFIN

(71) Applicant: Inner Mongolia Yitai Coal-based New Materials Research Institute Co., Ltd., Erdos (CN)

(72) Inventors: Tong Liu, Erdos (CN); Zhen Qian, Erdos (CN); Zhifei Li, Erdos (CN); Xiaolong Zhang, Erdos (CN); Yanpeng Xu, Erdos (CN); Gang Wang, Erdos (CN); Taishan Li, Erdos (CN); Hongyu Liu, Erdos (CN); Qiang Xue, Erdos (CN); Xu Wang, Erdos (CN)

(73) Assignee: Inner Mongolia Yitai Coal-based New Materials Research Institute Co., Ltd., Erdos (CN)

( * ) Notice: Subject to any disclaimer, the term of this patent is extended or adjusted under 35 U.S.C. 154(b) by 294 days.

(21) Appl. No.: 18/555,179

(22) PCT Filed: Dec. 9, 2022

(86) PCT No.: PCT/CN2022/138024
§ 371 (c)(1),
(2) Date: Oct. 12, 2023

(87) PCT Pub. No.: WO2024/108672
PCT Pub. Date: May 30, 2024

(65) Prior Publication Data
US 2025/0091971 A1 Mar. 20, 2025

(30) Foreign Application Priority Data
Nov. 24, 2022 (CN) ........................ 202211482757.X

(51) Int. Cl.
*C07C 7/08* (2006.01)

(52) U.S. Cl.
CPC ...................................... *C07C 7/08* (2013.01)

(58) Field of Classification Search
None
See application file for complete search history.

(56) References Cited

U.S. PATENT DOCUMENTS 2,455,803 A * 12/1948 Pierotti ..................... C07C 7/08
203/84
3,401,112 A * 9/1968 Dunlop .................. C07C 7/156
208/323
(Continued)

FOREIGN PATENT DOCUMENTS

CN 103232313 A 8/2013
CN 113402356 A 9/2021
(Continued)

OTHER PUBLICATIONS

Zubir et al. "Systematic design of energy efficient extractive distillation column for azeotrope mixture" Energy Procedia 142 (2017) 2636-2641 (Year: 2017).*

*Primary Examiner* — Renee Robinson
*Assistant Examiner* — Alyssa L Cepluch
(74) *Attorney, Agent, or Firm* — Myers Bigel, P.A.

(57) ABSTRACT

The present disclosure provides an α-olefin extractant and a method for separating an alkane and an α-olefin, wherein the α-olefin extractant comprises an alcohol-amine, a saturated monoketone having a carbon chain length of 7-10 and a monovalent salt of a Group IB metal, wherein the alcohol-amine, the saturated monoketone having a carbon chain length of 7-10 and the monovalent salt of a Group IB metal are in a mass ratio of (0.9-2.0):(0.8-1.5):(0.1-0.6). In the present disclosure, the technical principle of complexing extractive rectification is utilized and achieves the purpose of separating an olefin from an alkane by adding a complexing extractant to form a relatively stable complex
(Continued)

between a metals and the olefin. The present disclosure has advantages of good separation effect and high product yield.

17 Claims, 1 Drawing Sheet

(56) References Cited

U.S. PATENT DOCUMENTS

| | | | | |
|---|---|---|---|---|
| 4,686,317 | A * | 8/1987 | Quann | C10G 21/00 585/860 |
| 2003/0125599 | A1* | 7/2003 | Boudreau | C07C 7/152 585/809 |

FOREIGN PATENT DOCUMENTS

| | | | |
|---|---|---|---|
| CN | 114478169 | A | 5/2022 |
| EP | 3428142 | A1 | 1/2019 |

* cited by examiner

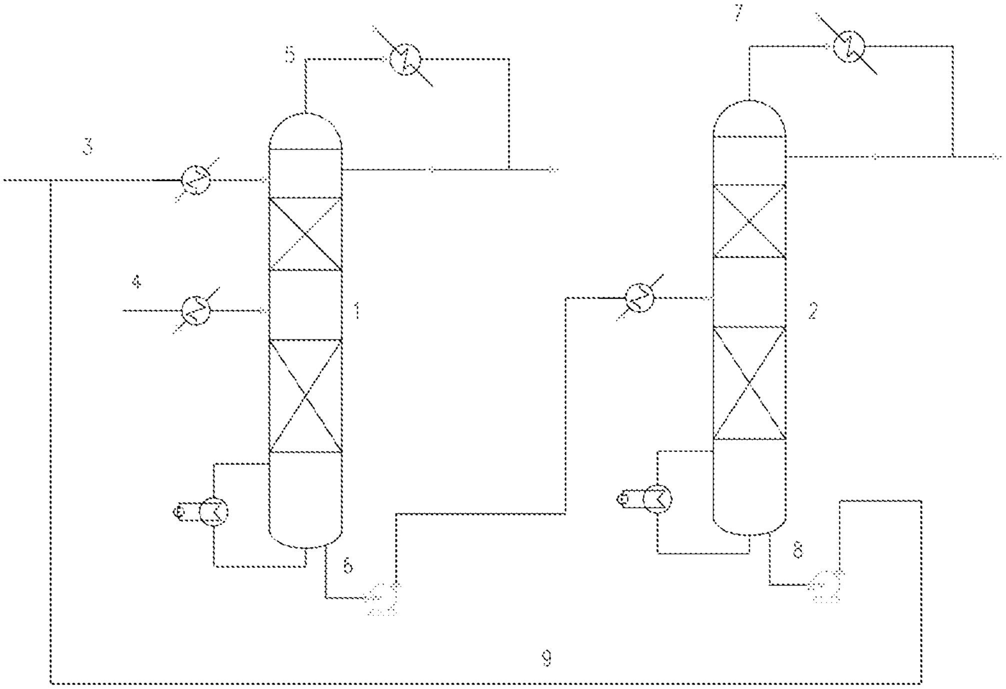
7
5
3
4
1
2
6
8
9

α-OLEFIN EXTRACTANT AND METHOD FOR SEPARATING AN ALKANE AND AN α-OLEFIN

CROSS REFERENCE TO RELATED APPLICATION

The present application is a 35 U.S.C. 371 national stage application of PCT International Application No. PCT/CN2022/138024 filed on Dec. 9, 2022, which claims a priority of Chinese Patent Application No. 202211482757.X, filed on Nov. 24, 2022 with a title of "α-Olefin extractant and method for separating an alkane and an α-olefin", each of which is incorporated herein by reference in their entireties.

TECHNICAL FIELD

The present disclosure relates to the technical field of separation technology, and particularly to an α-olefin extractant and a method for separating an alkane and an α-olefin.

BACKGROUND

Long chain α-olefins are important industrial chemicals, and are widely used in the fields such as surfactants, oil field chemicals, olefin copolymers, plasticizing alcohols, and lubricating oils. Currently, because of the problems in the production process, the production of long chain α-olefins is not high, and the demand for this raw material exceeds the supply, so that the fine chemical industry of long chain α-olefins finally can only partially import the raw material or give up development due to the too large gap and very high import price. Fischer-Tropsch (F-T) synthetic oils contain abundant long chain α-olefins, and there is large productivity of coal-based F-T synthetic oils, so it is a primary technical problem to seek a method for separating a high purity long chain α-olefin from a F-T oil crude product.

Fischer-Tropsch synthesis is a reaction where syngas ($CO+H_2$) is used as a raw material to produce liquid hydrocarbons, oxygenated compounds, carbon dioxide and water under the action of a catalyst. Fischer-Tropsch synthesis may indirectly convert a carbon-containing resource such as coal, natural gas and biomass to a liquid fuel, which has great practical significance on the balance of the "rich in coal, lean in oil, and less in gas" energy structure in our country. It is suggested in the literature by Wang Yadong et al. that the main products of a high temperature Fischer-Tropsch synthesis comprises fuel oils, oxygenated organic chemicals and olefins; the extraction of α-olefins with single carbon number or a certain range of carbon number from olefins with high content and continuous distribution of carbon numbers through an effective separation technology may not only replace conventional processes such as wax cracking, ethylene oligomerization and alkane dehydrogenation to produce olefins, but also facilitate the downstream diversified development of the Fischer-Tropsch products; the separation of high purity long chain α-olefins from a F-T synthetic oil may not only achieve high value-added long chain α-olefins, but also increase the economic benefits of the coal-based F-T synthetic oil.

Currently, main separation methods comprise the extractive rectification method, the composite film separation method, the adsorption method, and the like. Among them, the extractive rectification technology combines the advantages of both extraction and rectification operations, which greatly improves the efficiency in separating alkanes and olefins. The operation process is to continuously add a high boiling point additive to the top of the rectification column to change the relative volatility between the components in the feed liquid, so that the mixture which is difficult to be separated in a common rectification becomes easy to be separated. However, in current extractive rectification methods, a single organic solvent is mostly used as the extractant, resulting in large consumption and severe secondary pollution to the environment; or the extractant used is a combined solvent, but the yield of olefin products is very low, failing to satisfy the requirement on yield in practical industrial production. Thus, the selection of a suitable extractant is the key to whether the separation can be achieved. In the composite film separation method for separating olefins and alkanes, the manufacture of the composite film has relatively high cost, and is complicated to be implemented. The adsorption method has relatively stringent requirements on the specific surface area, pore volume and the like of the adsorbent. The adsorption separation process is likely to cause inactivation of the adsorbent with the accumulation of harmful substances in the feed, resulting in reduced production capacity and easy adsorption saturation. Also, the regenerative desorption process typically requires high temperature and consumes heat. The reactive distillation has relatively stringent requirements, for example, when comparing the main reaction time and the rectification time, the main reaction time may not be too long, otherwise the separation capacity of the rectification column cannot be fully utilized.

In view of this, the present disclosure is proposed.

SUMMARY

An object of the present disclosure comprises, for example, providing an α-olefin extractant and a method for separating an alkane and an α-olefin, which can overcome the problem of relatively strict requirements of conventional rectification.

The embodiments of the present disclosure may be implemented as follows.

In a first aspect, the present disclosure provides an α-olefin extractant comprising an alcohol-amine, a saturated monoketone having a carbon chain length of 7-10 and a monovalent salt of a Group IB metal, wherein the alcohol-amine, the saturated monoketone having a carbon chain length of 7-10 and the monovalent salt of a Group IB metal are in a mass ratio of (0.9-2.0):(0.8-1.5):(0.1-0.6).

In an optional embodiment, the alcohol-amine is at least one selected from the group consisting of monoethanol-amine, diethanol-amine and triethanol-amine.

In an optional embodiment, the organic ketone is at least one selected from the group consisting of 2-heptanone, sec-octanone, 2-nonanone and 3-decanone.

In an optional embodiment, the monovalent salt of a Group IB metal comprises at least one selected from the group consisting of cuprous chloride, cuprous tetrafluoroborate, silver tetrafluoroborate, cuprous trifluoroacetate, silver trifluoroacetate, cuprous acetate, silver acetate and silver nitrate.

In a second aspect, the present disclosure provides a method for separating an alkane and an α-olefin, comprising steps of:

- extractive rectification: subjecting a raw material containing an alkane and an α-olefin to extractive rectification with the extractant according to any one of preceding embodiments to obtain a raffinate and a rich solvent containing the α-olefin; and refining: subjecting the rich solvent containing the α-olefin to rectification to obtain the extractant and the isolated α-olefin.

In an optional embodiment, the raw material containing an alkane and an α-olefin is a Fischer-Tropsch synthetic oil; and preferably, the Fischer-Tropsch synthetic oil is firstly subjected to deacidification and deoxygenation before extraction; and preferably, the raw material contains 20-25 parts by weight of alkane and 70-75 parts by weight of α-olefin.

In an optional embodiment, the step of extractive rectification is performed in an extractive rectification column, and the step of refining is performed in a refining column, wherein the extractive rectification column and/or the refining column have a pressure in a range of 45-56 kPa and a temperature in a range of 45-125° C.;

preferably, the extractive rectification column and/or refining column have a temperature in a range of 45-65° C.; more preferably, the extractive rectification column has a bottom temperature in a range of 55-59° C., and the refining column has a bottom temperature in a range of 58-62° C.;

preferably, the extractive rectification column and/or refining column have a temperature in a range of 75-95° C.; more preferably, the extractive rectification column has a bottom temperature in a range of 84-88° C., and the refining column has a bottom temperature in a range of 87-91° C.; and preferably, the extractive rectification column and/or refining column have a temperature in a range of 95-125° C.; more preferably, the extractive rectification column has a bottom temperature in a range of 110-114° C., and the refining column has a bottom temperature in a range of 113-117° C.

In an optional embodiment, operation parameters in the extractive rectification column comprise: a plate number in a range of 34-36, a raw material feeding position at plates 24-26, an extractant feeding position at plates 3-5, a reflux ratio in a range from 3.3:1 to 3.7:1, and a mass ratio of extractant to raw material in a range from 2.5:1 to 3.5:1; and preferably, the operation parameters in the extractive rectification column comprise: a plate number of 35, a raw material feeding position at plate 25, an extractant feeding position at plate 4, a reflux ratio of 3.5:1, and a mass ratio of extractant to raw material of 3:1.

In an optional embodiment, operation parameters in the refining column comprise: a plate number in a range of 39-41, a feeding position at plates 27-29, and a reflux ratio in a range from 2.5:1 to 3.5:1; and preferably, the operation parameters in the refining column comprise: a plate number of 40, a feeding position at plate 28, and a reflux ratio of 3:1.

In an optional embodiment, the raw material and the extractant are preheated before entering the extractive rectification column, wherein the raw material is preheated to 65-100° C., and the extractant is preheated to 55-85° C.;

preferably, the raw material and the extractant are preheated before entering the extractive rectification column, wherein the raw material is preheated to 68-72° C., and the extractant is preheated to 58-62° C.; and preferably, the raw material and the extractant are preheated before entering the extractive rectification column, wherein the raw material is preheated to 93-97° C., and the extractant is preheated to 78-82° C.

BRIEF DESCRIPTION OF DRAWINGS

To more clearly illustrate the technical solutions in the embodiments of the present disclosure, the drawings to be used in the description of the embodiments will be briefly introduced below. It should be understood that the drawings below only show some embodiments of the present disclosure, and should not be regarded as limiting the scope. Other related drawings can be obtained by those skilled in the art according to these drawings without inventive efforts.

FIG. 1 is a schematic structural diagram of an apparatus for separating an alkane and an α-olefin in the embodiments of the present disclosure.

Reference numbers: 1—extractive rectification column; 2—refining column; 3—pipeline C; 4—pipeline D; 5—pipeline E; 6—pipeline F; 7—pipeline G; 8—pipeline H; 9—pipeline I.

DETAILED DESCRIPTION

The embodiments of the present disclosure have advantageous effects for example comprising the following ones.

The technical principle of complexing extractive rectification is utilized and achieves the purpose of separating an olefin from an alkane by adding a complexing extractant to form a relatively stable complex between a metal and the olefin.

As compared to conventional single organic extractant, the method of the present disclosure has advantages of easy operation, less amount of organic solution, less pollution to the environment, better separation effect, higher product yield, lower cost, and higher economic benefit, and will play an important role in separating alkanes from olefins.

In order to make the objects, technical solutions and advantages of the present disclosure more clear, the technical solutions of the embodiments of the present disclosure will be described in detail below with reference to the drawings of the embodiments of the present disclosure. Obviously, the embodiments described are only a part of, not all of the embodiments of the present disclosure. The components of the embodiments of the present disclosure as described and shown in the drawings here may be arranged and designed in various configurations.

Therefore, the detailed description of the embodiments of the present disclosure provided in the drawings below is not intended to limit the protection scope of the present disclosure, but merely represents selected embodiment of the present disclosure. All of other embodiments obtained by those skilled in the art based on the embodiments of the present disclosure without inventive efforts fall within the protection scope of the present disclosure.

It should be noted that like reference numbers and letters represents like elements in the drawing below. Therefore, once an element is defined in one FIGURE, it needs not to be further defined and explained in subsequent FIGURES.

In the description of the present disclosure, it should be noted that direction or position relationship indicated by the term "above", "below", "in", "out" or the like is the direction or position relationship as shown in the drawings, or the direction or position relationship in which the product of the present disclosure is conventionally placed in use, and it is only for the purpose of describing the present disclosure conveniently and simplifying the description, but it does not indicate or imply that the referred device or member must have a particular direction or position, or be constructed or operated in a particular direction or position. As a result, it should not be interpreted as limiting the present disclosure.

Furthermore, the term "first", "second" or the like is only used for distinguishing between descriptions, but cannot be understood as indicating or implying relative importance.

It should be noted that, unless contradiction, the features in the embodiments of the present disclosure can be combined with each other.

An embodiment of the present disclosure provides an α-olefin extractant comprising an alcohol-amine, a saturated monoketone having a carbon chain length of 7-10 and a monovalent salt of a Group IB metal, wherein the alcohol-amine, the saturated monoketone having a carbon chain length of 7-10 and the monovalent salt of a Group IB metal are in a mass ratio of (0.9-2.0):(0.8-1.5):(0.1-0.6).

In the present disclosure, the technical principle of complexing extractive rectification is utilized and forms a relatively stable complex between a metal and the olefin by adding a complexing extractant, thereby increasing the separation selectivity and reducing the use of organic solution. The metal used is a monovalent salt of a Group IB metal, d electrons of the ion occupying the 4d orbit feedback electrons to the *π-2p antibonding orbital of the olefin, thereby forming a Π bond. With an electron configuration of $(n-1)d^{10}ns^{0}$, it is not only easy to accept electrons but also easy to donor excessive d electrons, so it is a suitable olefin carrier.

In the embodiments of the present disclosure, the composition of the extractant is optimized, and an α-olefin having a purity up to 99.8% may be obtained.

In another possible embodiment, the alcohol-amine is at least one selected from the group consisting of monoethanol-amine, diethanol-amine and triethanol-amine.

In another possible embodiment, the organic ketone is at least one selected from the group consisting of 2-heptanone, sec-octanone, 2-nonanone and 3-decanone.

In another possible embodiment, the monovalent salt of a Group IB metal comprises at least one selected from the group consisting of cuprous chloride, cuprous tetrafluoroborate, silver tetrafluoroborate, cuprous trifluoroacetate, silver trifluoroacetate, cuprous acetate, silver acetate and silver nitrate.

In view of the cost of the catalyst, it is preferred to select the monovalent salts of copper and silver from the Group IB metals. It is preferable to select the monovalent salt of a Group IB metal with a higher ionization degree, because the monovalent metal cation thereof has higher degree of freedom, which may increase the complexation times between the monovalent metal cation and the olefin. It is more preferable to select cuprous tetrafluoroborate, cuprous trifluoroacetate and cuprous acetate.

Another embodiment of the present disclosure provides a method for separating an alkane and an α-olefin, comprising steps of:

- extractive rectification: subjecting a raw material containing an alkane and an α-olefin to extractive rectification with the extractant according to any one of preceding embodiments to obtain a raffinate and a rich solvent containing the α-olefin; and
- refining: subjecting the rich solvent containing the α-olefin to rectification to obtain the extractant and the isolated α-olefin. In another possible embodiment, the raw material containing an alkane and an α-olefin is a Fischer-Tropsch synthetic oil.

In another possible embodiment, the Fischer-Tropsch synthetic oil is firstly subjected to removal of acids and removal of oxygenated compounds before extraction.

In another possible embodiment, the raw material contains 20-25 parts by weight of alkane and 70-75 parts by weight of α-olefin.

In the present disclosure, the deacidified and deoxygenated Fischer-Tropsch synthetic oil (from Inner Mengolia Yinuo New Material Co. Ltd.), i.e., a mixture of hydrocarbons with single carbon numbers, is used as the raw material, and the main composition of the raw material before and after deacidification and deoxygenation is shown in Table 1. By using the method of the present disclosure, the separation of alkane and olefin components may be achieved efficiently and rapidly, obtaining α-olefin products with high purity, wide applicability, low cost and high economy. This will break the monopoly of foreign α-olefins, and greatly accelerate the rapid development and wide application of high-value-added products such as downstream high-end synthetic resins and top lubricants in our country.

TABLE 1 the composition of a coal-based Fischer-Tropsch synthetic oil

| Components | Before deacidification and deoxygenation | After deacidification and deoxygenation |
|---|---|---|
| Alkanes | 21.13 wt % | 22.8 wt % |
| Olefins | 70.87 wt % | 73.6 wt % |
| Acids | 0.8 wt % | — |
| Other oxygenated compounds | 5.2 wt % | <1 ppm |

In another possible embodiment, the step of extractive rectification is performed in an extractive rectification column, and the step of refining is performed in a refining column, wherein the extractive rectification column and/or the refining column have a pressure in a range of 45-56 kPa and a temperature in a range of 45-125° C.

In another possible embodiment, the extractive rectification column and/or refining column have a temperature in a range of 45-65° C.; more preferably, the extractive rectification column has a bottom temperature in a range of 55-59° C., and the refining column has a bottom temperature in a range of 58-62° C., which may be used for isolating α-olefins having a carbon chain length of 6 separately.

In another possible embodiment, the extractive rectification column and/or refining column have a temperature in a range of 75-95° C.; more preferably, the extractive rectification column has a bottom temperature in a range of 84-88° C., and the refining column has a bottom temperature in a range of 87-91° C., which may be used for isolating α-olefins having a carbon chain length of 7 separately.

In another possible embodiment, the extractive rectification column and/or refining column have a temperature in a range of 95-125° C.; more preferably, the extractive rectification column has a bottom temperature in a range of 110-114° C., and the refining column has a bottom temperature in a range of 113-117° C., which may be used for isolating α-olefins having a carbon chain length of 8 separately.

In another possible embodiment, operation parameters in the extractive rectification column comprise: a plate number in a range of 34-36, a raw material feeding position at plates 24-26, an extractant feeding position at plates 3-5, a reflux ratio in a range from 3.3:1 to 3.7:1, and a mass ratio of extractant to raw material in a range from 2.5:1 to 3.5:1.

In another possible embodiment, the operation parameters in the extractive rectification column comprise: a plate number of 35, a raw material feeding position at plate 25, an extractant feeding position at plate 4, a reflux ratio of 3.5:1, and a mass ratio of extractant to raw material of 3:1.

In another possible embodiment, the operation parameters in the refining column comprise: a plate number in a range of 39-41, a feeding position at plates 27-29, and a reflux ratio in a range from 2.5:1 to 3.5:1.

In another possible embodiment, the operation parameters in the refining column comprise: a plate number of 40, a feeding position at plate 28, and a reflux ratio of 3:1.

In another possible embodiment, the raw material and the extractant are preheated before entering the extractive rectification column, wherein the raw material is preheated to 65-100° C., and the extractant is preheated to 55-85° C.

In another possible embodiment, the raw material and the extractant are preheated before entering the extractive rectification column, wherein the raw material is preheated to 68-72° C., and the extractant is preheated to 58-62° C., which may be used for isolating α-olefins having a carbon chain length of 7 separately.

In another possible embodiment, the raw material and the extractant are preheated before entering the extractive rectification column, wherein the raw material is preheated to 93-97° C., and the extractant is preheated to 78-82° C., which may be used for isolating α-olefins having a carbon chain length of 8 separately.

The features and performances of the present disclosure will be described in further detail below with reference to Examples.

The method for separating an alkane and an α-olefin of the present disclosure comprises the following steps.

Preparation of experimental chemicals and apparatuses: ethanol-amine, 2-heptanone, cuprous chloride, an extractive rectification column, a refining column, and a heat exchanger.

Operation Steps:

In the present experiment, the raw material was a coal-based Fischer-Tropsch oil which was pretreated for deoxygenation, deacidification and cutting, i.e., a mixture containing olefins and alkanes to be separated, and the target α-olefin had a carbon chain length of n where 6≤n≤8.

When the apparatus as shown in FIG. 1 was used to isolate α-olefins with a carbon chain length of 6 separately, the components to be separated entered the extractive rectification column 1 at a lower middle portion via the pipeline D4, and the combined extractant entered the extractive rectification column 1 at an upper portion via the pipeline C3, where heat was provided to the bottom by a reboiler. After the extractive rectification, the olefins were dissolved in the combined extractant, and the alkanes were discharged from the top of the extractive rectification column 1 via the pipeline E5, where a portion of the alkanes were flowed back into the extractive rectification column 1 at an upper portion, the other portion of the alkanes were withdrawn. The rich solvent containing the olefins was withdrawn from the bottom of the extractive rectification column 1, and entered the refining column 2 at the middle portion via the pipeline F6, where heat is provided to the bottom by a reboiler. The olefins were separated from the combined extractant through rectification. The olefins were discharged from the top of the refining column 2 via the pipeline G7, where a portion of the olefins were flowed back into the refining column 2 at an upper portion, and the other portion of the olefins were withdrawn. The extractant was discharged from the bottom of the refining column 2 via the pipeline H8, passed through the pipeline I9, and then returned back to the extractive rectification column 1 for recycling.

Here, n=6, the extractant was formulated at an optimum ethanol-amine:2-heptanone:cuprous chloride ratio of 1:1:0.2; the operation parameters for the extractive rectification column comprised: a bottom temperature of 57° C., an operating pressure of 55.3 kPa, a plate number of 35, a raw material feeding position of 25, an extractant feeding position of 4, a reflux ratio of 3.5:1, and a mass ratio of extractant to raw material of 3:1; the operation parameters for the refining column comprised: a bottom temperature of 60° C., an operating pressure of 55.3 kPa, a plate number of 40, a raw material feeding position of 28, and a reflux ratio of 3:1. The recovered olefins had a purity of 99.8 wt % or more.

When the apparatus as shown in FIG. 1 was used to isolate α-olefins with a carbon chain length of 7 separately, the components to be separated were heated to 70° C. by a preheater via the pipeline D4, and entered the extractive rectification column 1 at a lower middle portion, and the combined extractant was heated to 60° C. by a preheater via the pipeline C3, and entered the extractive rectification column 1 at an upper portion, where heat was provided to the bottom by a reboiler. After the extractive rectification, the olefins were dissolved in the combined extractant, and the alkanes were discharged from the top of the extractive rectification column 1 via the pipeline E5, where a portion of the alkanes were flowed back into the extractive rectification column 1 at an upper portion, the other portion of the alkanes were withdrawn. The rich solvent containing the olefins was withdrawn from the bottom of the extractive rectification column 1, and entered the refining column 2 at the middle portion via the pipeline F6, where heat is provided to the bottom by a reboiler. The olefins were separated from the combined extractant through rectification. The olefins were discharged from the top of the refining column 2 via the pipeline G7, where a portion of the olefins were flowed back into the refining column 2 at an upper portion, and the other portion of the olefins were withdrawn. The extractant was discharged from the bottom of the refining column 2 via the pipeline H8, passed through the pipeline I9, and then returned back to the extractive rectification column 1 for recycling.

Here, n=7, the extractant was formulated at an optimum ethanol-amine:2-heptanone:cuprous chloride ratio of 1:1:0.2; the operation parameters for the extractive rectification column comprised: a bottom temperature of 86° C., an operating pressure of 55.3 kPa, a plate number of 35, a raw material feeding position of 25, an extractant feeding position of 4, a reflux ratio of 3.5:1, and a mass ratio of extractant to raw material of 3:1; the operation parameters for the refining column comprised: a bottom temperature of 89° C., an operating pressure of 55.3 kPa, a plate number of 40, a raw material feeding position of 28, and a reflux ratio of 3:1. The recovered olefins had a purity of 99.8 wt % or more.

When the apparatus as shown in FIG. 1 was used to isolate α-olefins with a carbon chain length of 8 separately, the components to be separated were heated to 95° C. by a preheater via the pipeline D4, and entered the extractive rectification column 1 at a lower middle portion, and the combined extractant was heated to 80° C. by a preheater via the pipeline C3, and entered the extractive rectification column 1 at an upper portion, where heat was provided to the bottom by a reboiler. After the extractive rectification, the olefins were dissolved in the combined extractant, and the alkanes were discharged from the top of the extractive rectification column 1 via the pipeline E5, where a portion of the alkanes were flowed back into the extractive rectification column 1 at an upper portion, the other portion of the alkanes were withdrawn. The rich solvent containing the olefins was withdrawn from the bottom of the extractive rectification column 1, and entered the refining column 2 at the middle portion via the pipeline F6, where heat is provided to the bottom by a reboiler. The olefins were separated from the combined extractant through rectification. The olefins were discharged from the top of the refining column 2 via the pipeline G7, where a portion of the olefins were flowed back into the refining column 2 at an upper portion, and the other portion of the olefins were withdrawn. The extractant was discharged from the bottom of the refining column 2 via the pipeline H8, passed through the pipeline I9, and then returned back to the extractive rectification column 1 for recycling.

Here, n=8, the extractant was formulated at an optimum ethanol-amine:2-heptanone:cuprous chloride ratio of 1:1:0.2; the operation parameters for the extractive rectification column comprised: a bottom temperature of 112° C., an operating pressure of 55.3 kPa, a plate number of 35, a raw material feeding position of 25, an extractant feeding position of 4, a reflux ratio of 3.5:1, and a mass ratio of extractant to raw material of 3:1; the operation parameters for the refining column comprised: a bottom temperature of 115° C., an operating pressure of 55.3 kPa, a plate number of 40, a raw material feeding position of 28, and a reflux ratio of 3:1. The recovered olefins had a purity of 99.8 wt % or more.

It should be noted that the numerical values in the operation parameters may slightly vary within a tolerable error range due to the control precision of the apparatus, which will have an effect on the result within a controllable range.

TABLE 2 the effect of various extractant proportions on the product

| No. | n | Extractant proportions | Condition parameters in the extractive rectification column | Condition parameters in the refining column | Product purity | Product yield |
|---|---|---|---|---|---|---|
| 1 | 6 | 1:1:0.2 | Bottom temperature: 57° C., operating pressure: 55.3 kPa, plate number: 35, raw material feeding position: 25, extractant feeding position: 4, reflux ratio: 3.5:1, mass ratio of extractant to raw material: 3:1 | Bottom temperature: 60° C., operating pressure: 55.3 kPa, plate number: 40, feeding position: 28, reflux ratio: 3:1 | 99.8 wt % | 82.7 |
| 2 | | 0.9:1.5:0.1 | | | 82 wt % | 87.7 |
| 3 | | 2.0:0.8:0.6 | | | 86 wt % | 86.3 |
| 4 | | 0.5:1:1 | | | 75 wt % | 89.2 |
| 5 | | 1:2:1 | | | 70 wt % | 93.9 |
| 6 | | 0.8:0.7:1 | | | 72 wt % | 91.9 |
| 7 | 7 | 1:1:0.2 | Raw material prehated to 70° C., extractant preheated to 60° C., bottom temperature: 86° C., operating pressure: 55.3 kPa, plate number: 35, raw material feeding position: 25, extractant feeding position: 4, reflux ratio: 3.5:1, mass ratio of extractant to raw material: 3:1; | Bottom temperature: 89° C., operating pressure: 55.3 kPa, plate number: 40, feeding position: 28, reflux ratio: 3:1 | 99.8 wt % | 81.2 |
| 8 | | 0.9:1.5:0.1 | | | 81 wt % | 86.7 |
| 9 | | 2.0:0.8:0.6 | | | 83 wt % | 85.2 |
| 10 | | 0.5:1:1 | | | 75 wt % | 88.6 |
| 11 | | 1:2:1 | | | 70 wt % | 93 |
| 12 | | 0.8:0.7:1 | | | 72 wt % | 91.6 |
| 13 | 8 | 1:1:0.2 | Raw material prehated to 95° C., extractant preheated to 80° C., bottom temperature: 112° C., operating pressure: 55.3 kPa, plate number: 35, raw material feeding position: 25, extractant feeding position: 4, reflux ratio: 3.5:1, mass ratio of extractant to raw material: 3:1; | Bottom temperature: 115° C., operating pressure: 55.3 kPa, plate number: 40, feeding position: 28, reflux ratio: 3:1 | 99.8 wt % | 80.6 |
| 14 | | 0.9:1.5:0.1 | | | 82 wt % | 85.1 |
| 15 | | 2.0:0.8:0.6 | | | 86 wt % | 84.9 |
| 16 | | 0.5:1:1 | | | 75 wt % | 88.4 |
| 17 | | 1:2:1 | | | 70 wt % | 92.3 |
| 18 | | 0.8:0.7:1 | | | 72 wt % | 90.8 |

Notes:
the extractant proportion is the mass ratio of ethanol-amine: 2-heptanone: cuprous chloride, and the extractant proportions in subsequent examples and comparative examples have the same meaning.

Comparative Example 1

Comparative Example 1 differs from the first group of experiments merely in that the alcohol-amine solution is removed from the combined solution, and the combined extractant only consisted of the organic ketone and the metal salt, thereby obtaining a product having a purity of 80 wt % at a yield of 4%. Comparative Example 2

Comparative Example 2

Comparative Example 2 differs from the first group of experiments merely in that the organic ketone solution is removed from the combined solution, and the combined extractant only consisted of the alcohol-amine and the metal salt, thereby obtaining a product having a purity of 86 wt % at a yield of 19%.

The above embodiments are only particular embodiments of the present disclosure, but the protection scope of the present disclosure is not limited thereto. Within the technical scope disclosed in the present disclosure, one skilled in the art may readily envisage variations or alternatives, and all of them are covered by the protection scope of the present disclosure. Therefore, the protection scope of the present disclosure should be defined by the appended claims.

What is claimed is:

1. An α-olefin extractant, comprising monoethanol-amine, 2-heptanone and cuprous chloride, wherein monoethanol-amine, 2-heptanone and cuprous chloride are in a mass ratio of (0.9-2.0):(0.8-1.5):(0.1-0.6).

2. A method for separating an alkane and an α-olefin, comprising steps of:

extractive rectification: subjecting a raw material containing an alkane and an α-olefin to extractive rectification with the extractant according to claim 1 to obtain a raffinate and a rich solvent containing the α-olefin; and refining: subjecting the rich solvent containing the α-olefin to rectification to obtain the extractant and the isolated α-olefin.

3. The method for separating an alkane and an α-olefin according to claim 2, wherein the raw material containing an alkane and an α-olefin is a Fischer-Tropsch synthetic oil; and the Fischer-Tropsch synthetic oil is firstly subjected to deacidification and deoxygenation before extraction.

4. The method for separating an alkane and an α-olefin according to claim 2, wherein the step of extractive rectification is performed in an extractive rectification column, and the step of refining is performed in a refining column, wherein the extractive rectification column and/or the refining column have a pressure in a range of 45-56 kPa and a temperature in a range of 45-125° C.

5. The method for separating an alkane and an α-olefin according to claim 4, wherein operation parameters in the extractive rectification column comprise: a plate number in a range of 34-36, a raw material feeding position at plates 24-26, an extractant feeding position at plates 3-5, a reflux ratio in a range from 3.3:1 to 3.7:1, and a mass ratio of extractant to raw material in a range from 2.5:1 to 3.5:1.

6. The method for separating an alkane and an α-olefin according to claim 4, wherein operation parameters in the refining column comprise: a plate number in a range of 39-41, a feeding position at plates 27-29, and a reflux ratio in a range from 2.5:1 to 3.5:1.

7. The method for separating an alkane and an α-olefin according to claim 4, wherein the raw material and the extractant are preheated before entering the extractive rectification column, wherein the raw material is preheated to 65-100° C., and the extractant is preheated to 55-85° C.

8. The method for separating an alkane and an α-olefin according to claim 3, wherein the raw material contains 20-25 parts by weight of alkane and 70-75 parts by weight of α-olefin.

9. The method for separating an alkane and an α-olefin according to claim 4, wherein the extractive rectification column and/or refining column have a temperature in a range of 45-65° C.

10. The method for separating an alkane and an α-olefin according to claim 9, wherein the extractive rectification column has a bottom temperature in a range of 55-59° C., and the refining column has a bottom temperature in a range of 58-62° C.

11. The method for separating an alkane and an α-olefin according to claim 4, wherein the extractive rectification column and/or refining column have a temperature in a range of 75-95° C.

12. The method for separating an alkane and an α-olefin according to claim 11, wherein the extractive rectification column has a bottom temperature in a range of 84-88° C., and the refining column has a bottom temperature in a range of 87-91° C.

13. The method for separating an alkane and an α-olefin according to claim 4, wherein the extractive rectification column and/or refining column have a temperature in a range of 95-125° C.

14. The method for separating an alkane and an α-olefin according to claim 13, wherein the extractive rectification column has a bottom temperature in a range of 110-114° C., and the refining column has a bottom temperature in a range of 113-117° C.

15. The method for separating an alkane and an α-olefin according to claim 5, wherein the operation parameters in the extractive rectification column comprise: a plate number of 35, a raw material feeding position at plate 25, an extractant feeding position at plate 4, a reflux ratio of 3.5:1, and a mass ratio of extractant to raw material of 3:1.

16. The method for separating an alkane and an α-olefin according to claim 6, wherein the raw material and the extractant are preheated before entering the extractive rectification column, wherein the raw material is preheated to 68-72° C., and the extractant is preheated to 58-62° C.

17. The method for separating an alkane and an α-olefin according to claim 6, wherein the raw material and the extractant are preheated before entering the extractive rectification column, wherein the raw material is preheated to 93-97° C., and the extractant is preheated to 78-82° C.

* * * * *